United States Patent [19]

Nimni et al.

[11] Patent Number: 5,374,539
[45] Date of Patent: Dec. 20, 1994

[54] PROCESS FOR PURIFYING COLLAGEN AND GENERATING BIOPROSTHESIS

[76] Inventors: Marcel E. Nimni; David T. Cheung, both of Children's Hospital Los Angeles P.O. Box 54700, Los Angeles, Calif. 90054-0700

[21] Appl. No.: 716,091

[22] Filed: Jun. 17, 1991

[51] Int. Cl.$^5$ .................. A61K 31/78; A61B 17/00; C08H 1/06; C09H 1/04
[52] U.S. Cl. .................. 435/68.1; 530/356; 530/410; 530/322; 530/323
[58] Field of Search .............. 530/356, 410, 322, 323

[56] References Cited

U.S. PATENT DOCUMENTS

| | | | |
|---|---|---|---|
| 3,742,955 | 7/1973 | Battista et al. | 608/214 |
| 4,050,893 | 9/1977 | Hancock et al. | 8/94.11 |
| 4,098,571 | 7/1978 | Miyata et al. | 422/100 |
| 4,120,649 | 10/1978 | Schecter | 8/94.11 |
| 4,140,537 | 2/1979 | Luck et al. | 530/356 |
| 4,215,200 | 7/1980 | Miyata et al. | 530/356 |
| 4,220,724 | 9/1980 | Berg et al. | 435/273 |
| 4,268,131 | 5/1981 | Miyata et al. | 530/356 |
| 4,280,954 | 7/1981 | Yannas et al. | 530/356 |
| 4,383,832 | 5/1983 | Fraefel et al. | 8/94.11 |
| 4,400,833 | 8/1983 | Kurland | 623/13 |
| 4,713,466 | 12/1987 | DeVone et al. | 530/356 |
| 4,755,593 | 7/1988 | Lauren | 530/356 |

OTHER PUBLICATIONS

Nimni, M. E. et al. "Collagen: Biochemistry Biomechanics and Biotechnology", M. E. Nimni (editor) CRC Press, Boca Raton, Fla., vol. III pp. 1-38, 1988.
Nimni, "Collagen Structure and Function",in Encyclopedia of Human Biology, Academic Press, Inc. vol. 2, 559-573, Mar. 1991.
Nimni et al., "Chemistry Modified Collagen: A Vacsual Biomaterial for Tissue Replacement", J. Biomedical Materials Research vol. 21, 741-777 (1987).
Weadock et al., "Evaluation of Collagen Cross-Linking Techniques", Biomat. Mat. Dev., Art. Org., 11(4)293-318 (1983-1984).
Nimini, M. E. "Collagen: Structure, Function and Metabolism in Nouural and Fibrotic Tissues", Seminars in Arthritis and Rheumatism vol. XIII, No. 1, Aug., (1983).
Cheung et al., "The Effect of Y-irradiation on collagen molecules, isolated & chains, and cross-filled native fibers", J. of Biomed Mal. Res. vol. 24, 581-589 (1990).
Kato et al. "Mechanical Properites of Collagen Fibers: A Comparison of Reconstituted and Rat Tail tendon Fibers", Biomaterials, vol. 10, Jan. (1989).

*Primary Examiner*—Howard E. Schain
*Assistant Examiner*—Lynn Touzeau
*Attorney, Agent, or Firm*—Poms, Smith, Lande & Rose

[57] ABSTRACT

A process is described to purify collagen fibers while allowing the individual constituent molecules to retain their native configuration and 3-dimensional arrangement characteristic of the tissues from which they are derived. Collagenous tissues used as sources of purified collagen and for manufacturing bioprosthesis contain significant amounts of other substances (elastin, glycoproteins, polysaccharides, cell derived materials, etc.). This process becomes therefore useful to selectively preserve the collagen in its native conformation and to eliminate contaminants. The method described allows for enzymatic removal of all extraneous materials while preserving the native collagen molecules in their original fiber configuration. Subsequently this network of native collagen fibrils can be crosslinked using standard bifunctional crosslinking reagents, treated with other chemical substances, physical methods of insolubilization, or can be disrupted chemically or mechanically into smaller molecular aggregates or into the constituent single molecules.

11 Claims, 1 Drawing Sheet

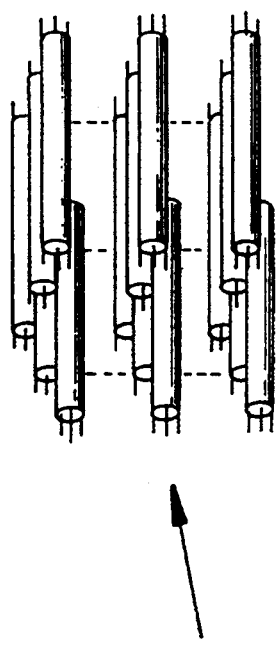
FIG. IC
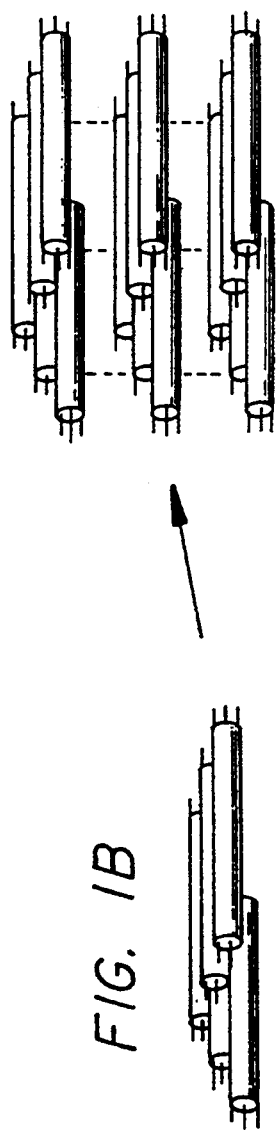
FIG. ID
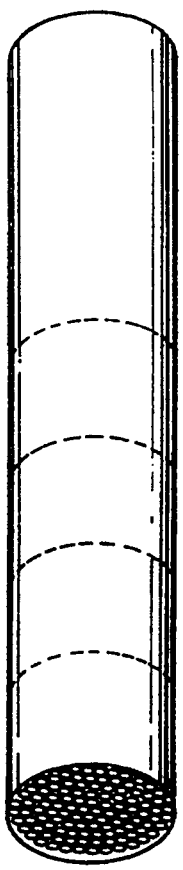
FIG. IE
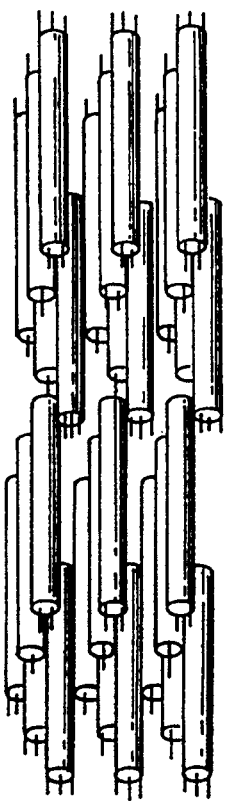
FIG. IB
FIG. IA

PROCESS FOR PURIFYING COLLAGEN AND GENERATING BIOPROSTHESIS

BACKGROUND

For many years now collagenous tissues have been a source of materials implanted as bioprosthesis, used on the surface of the body as tissue dressings, or as carriers in many biological applications. The source of such materials and the materials in question include porcine heart valves, bovine ligaments and tendons, bovine and human blood vessels, pericardial patches, demineralized bone matrix, suture materials made out of intestinal serosa or reconstituted collagen, among others. Collagen prepared from such tissues using various methods and exposed to various degrees of purification are used as hemostatic agents, tissue fillers and expanders, drug carriers, dermal substitutes, ophthalmic dressings, etc. The collagen in these preparations varies in its grade of purity, as well as in the degree in which it resembles the native configuration (molecular packing fiber orientation, fiber diameter) and retention of native configuration (triple-helix) found in the live tissue.

The native characteristics of the collagen network are summarized schematically in FIG. 1. The individual molecules, which appear as very long rods, are composed of 3 chains known as $\alpha$ chains. For such molecules to retain their fundamental biological properties it is essential that the 3 $\alpha$ chains remain in a triple helical conformation. The non helical regions which are attached to the ends of the molecules are not essential for this purpose, but can be rather detrimental for the application cited as they contribute very significantly to generate immunological problems. These non-helical regions, remain on the surface as well as buried within the fibers when such molecules assemble to form such fibers. Prior technology was unable to remove them without disrupting the fibrillar structure. In FIG. 1 these terminal extensions (telopeptides) are shown as appendages at the ends of the molecules.

The method described allows for enzymes to reach such arenas of the fibril and remove these non-helical extensions without dissociating the fibers into individual molecules and causing the fibrils to disassemble.

In essence, antigenic determinants can be removed, as well as other contaminating extraneous molecules, which exist between the collagen while leaving the fibrils essentially intact. Therefore such fibers will retain their original characteristics (i.e. diameter, length, orientation within the matrix, packing density, surface characteristics, etc.) such organization, identified as a native structure of configuration, is essential for the collagen network to exhibit its desired properties (i.e. mechanical function, structural support, cell surface compatibility, etc.).

In addition, it is essential for the individual molecules to also retain their native configuration (triple helix). Prior technology did not allow all of these features to be retained simultaneously, either one or another (native packing or molecular integrity) had to be lost. This invention allows for the essential characteristics of collagen to be retained.

In the prior art, when tissues such as porcine heart valves are used as bioprosthesis, the relevant area of the animal is explanted, crosslinked in its native configuration with agents such as glutaraldehyde or other crosslinking reagents, and after mounting on suitable stents, implanted into the host. Such implants contain not only the structural framework of collagen but large numbers of substances, not necessary for structural purposes but which are associated with the donor tissue, i.e. cells and cell debris, interfibrillar matrix, elastin, etc. Some of these substances are not as readily tanned as collagen and may preferentially leach out following implantation into the host, giving rise to a series of undesired reactions (i.e. immunological sensitization, foreign body tissue reaction, etc.).

In the prior art attempts were made to remove these contaminants without effecting the collagen framework but these have proven unsuccessful. Either the collagen becomes degraded or the telopeptide free molecules become dispersed in the solution. If the collagen is crosslinked prior to chemical or enzymatic removal of these noncollagenous substances, the collagen becomes irreversibly and to such impurities. The crosslinking reagents which do not selectively react with collagen, but also interact with many of these less desirable molecules, render them also insoluble and impossible to remove without disrupting the collagenous framework. The need to eliminate these noncollagenous substances while leaving behind the collagen fibrils in their native 3-dimensional configuration within the tissue is therefore well recognized. The method we describe provides the necessary scaffolding for such implants to function biomechanically in a tissue and organ compatible manner, but devoid of non-essential components.

In a corollary of the procedure developed, we have learned how to generate a purified collagenous network which can also serve as a source of purified collagen for a variety of uses.

Based on the method described the collagen can be formulated as a hemostatic agent with several intrinsic advantages over other collagenous materials devoted to similar use. It retains the native fibrillar characteristics, which are known to be essential for platelet aggregation to occur, the native fibrillar diameter and is devoid of other impurities that can hinder the recognition of the collagen surface by platelets, cells or other molecular species. A hemostatic agent as described here is a preparation of collagen which is able to aggregate platelets on its surface and initiate the process of clot formation.

A material can also be prepared which has ideal suture characteristics, and which is compatible with the process of wound healing. A surgical suture is a collagen derived material, which has thread like characteristics, which is derived from animal tissues such as intestinal serosa and which is used to close open wounds or repair organ defects. The material in question retains the desired mechanical properties, since the collagen framework is left intact by the treatment received, while impurities associated with the natural tissues have been removed. This makes the collagenous material much more biocompatible, and less likely to elicit the immunological response associated with the large number of immune related cells which populate wounded areas. The enzymatic treatment also renders the collagen more visible to tissue proteases and therefore allows for its more rapid removal. The removal of impurities which can mask reactive groups on collagen can allow the process of resorbtion of such sutures to be more adquately modulated by the process of crosslinking. The introduction of chemical crosslinks can therefore be performed in a much more controlable fashion.

In essence, the process described generates a purified network of collagen which can be crosslinked using standard bifunctional agents or other forms of crosslinking methods, or can be used as a starting material for the purification of collagen in large amounts. In the latter case, the final product can present itself in the form of native fibrils or monomeric collagen after suitable dispersion of the collagenous network. The fact that one can retain the native collagenous framework, in its 3-dimensional array devoid of surrounding non-collagenous materials is the essence of our discovery. This cannot be achieved by the prior art.

BRIEF DESCRIPTION OF THE DRAWING

FIGS. 1A, 1B, 1C, 1D, and 1E show how individual collagen molecules assemble into fibers with the non-helical extensions buried inside. These extensions, depicted by 3 small segments at either ends of the molecules, are removed by enzymes which can penetrate into the interstices of the fibers without disrupting the molecular packing.

FIG. 1A shows a collagen molecule with non-helical extensions at either end. FIG. 1B shows an aggregation of individual molecules to form microfibrils. FIG. 1C shows a lateral aggregation of these microfibrils, followed by FIG. 1D which shows end to end aggregation. Thence steps lead to the formation of collagen fibers shown in FIG. 1E, which can be clearly seen with the electron microscopy. Bundles of such fibers are visible under the light microscope. The present invention allows for the molecules to be retained in this native configuration throughout the purification process and in the final product.

SUMMARY OF THE INVENTION

Collagen, as mentioned, is synthesized as a precursor molecule called procollagen, which has long extensions that either end of the molecule. These extensions contain non-helical region which contributes little to the structural properties of the collagen fibers. After this procollagen molecule is synthesized, it is extruded out of the cell where through a natural enzymatic process, most of these non-helical extensions are removed. Just a few residues at either end are left behind and they are important in contributing to the formation of crosslinks between molecules. These remnants are important to this invention not only because they stabilize the fibrillar network but also because of interspecies variation and enzymatic availability they contribute to the immunogenicity of collagen. These non-helical areas at the ends of collagen are susceptible to enzymatic degradation and this property has been used in the past as a means of disassembling the fibrils in order to solubilize the molecules. In particularly pepsin, an acid pH, has been used for this purpose. Such an approach will yield significant amounts of soluble collagen from highly insoluble collagenous matrices, such as tendons or skin, commonly used as starting materials.

It has been discovered that performing these enzymatic digestions in the presence of high salt concentrations, which maintain the collagen molecules aggregated under the experimental conditions used, will still allow the enzymes to remove these undesirable remnants of the non-helical extensions present at either end of the molecule without disassembling the collagen fibrils. Therefore, by subjecting tissues such as tendons and skin to proteolytic enzymes in the presence of high levels of salt, we are able to achieve our goal, which is to remove these extensions while retaining not only the fibrillar assembly but also the 3-dimensional arrangement and packing of these fibers, thus preserving the actual shape, structure and function of the original tissue. In this way one is able not only to remove these extensions, but other proteins which, in contrast to the helical regions of the collagen molecule, are susceptible to degradation under the conditions used. Therefore, cellular proteins, interfibrillar proteins, and glycoproteins, residual serum proteins, and other extraneous materials are all digested and removed by this process leaving behind the helical region of collagen.

By maintaining these conditions which inhibit the depolymerization of the collagenous network, it has now become possible to rinse thoroughly our material to extract out the undesirable degradation products as well as the added enzymes. After achieving this objective, that is preserving the fibrillar collagen now devoid of extensions and crosslinks, it is possible to go in different directions. One can crosslink the fibrillar network with tanning reagents to preserve their structure, or one can decrease the ionic strength thus allowing the molecules to disperse into a suspensions of monomeric or polymeric collagen. The first of these approaches is used in the generation of collagen bioprosthesis which have now been cleared of the extraneous macromolecules which were entrapped in the interstices of the fibrillar network. It has been noted that such treated tissues become lighter in color and more pliable, an effect that is particularly evident after such matrices are crosslinked with bifunctional reagents such as glutaraldehyde (0.2% solution).

In the second instance, one can generate a purified collagen suspension which can be used as a starting material for preparing a variety of products which require the availability of highly purified monomeric collagen. This can be used as such or reconstituted into preparations of various shapes and sizes (powder, sheets, tubes, used for coating the surface of prosthesis, etc.).

In all instances this native collagen can be further stabilized using standard crosslinking methods.

DETAILED DESCRIPTION OF THE PREFERRED EMBODIMENTS

Exemplary starting materials useful in practicing the invention include: animal tissues of diverse origins, e.g. skin, heart valves, blood vessels, pericardia, dura mater, ligaments, tendons, intestinal serosa, and other collagenous materials. Assuming tissues are used, they are first cleaned from adherent fat or loose connective tissue as soon as possible after harvesting. Immediately thereafter they are placed in a balanced electrolyte solution that is calcium-free and buffered at a neutral pH with a phosphate buffer (0.2 to 0.01 Molar). This solution is kept cool (4°-8° C.).

A. Preparation of Purified Collagen

In the case of tendon, used as a preferred source of purified collagen, the rinsed tissue is frozen at −30° C. and cleaned of fat and adherent loose connective tissue. It is then stored in air tight containers.

In a typical preparation 500 g of such materials, cut mechanically into small pieces, is suspended in 2000 ml of 0.5M acetic acid containing 4 g of pepsin and 100 g of NaCl. The mixture is homogenized at high speed in a Stephen Mixer or equivalent for a total of 10 minutes keeping the temperature around 4° C. The resulting suspension is allowed to stand in the cold for 24 hrs. It is then centrifuged in a refrigerated centrifuge at 300 RPM for 30 minutes. The precipitates (pellet residues)

are collected and washed with 1000 ml 0.5M acetic acid containing 50 g of NaCl. After stirring for 10 minutes, the suspension is again centrifuged at 3000 RPM for 30 minutes. This step which removes most of the pepsin, is repeated twice. The final pellet is suspended in a phosphate buffered solution (0.05M, pH=7.0) containing 4.0M NaCl (approx. 24% w/vol NaCl), stirred for 10 minutes and centrifuged at 3000 RPM for 30 minutes. This step, which removes intact and digested glycoproteins and proteoglycans, is repeated twice.

Desalting and further purification is achieved by suspending the residue in 1 liter of a water - Isopropanol mixture (4:1) (20% IPA). This is followed by centrifugation. This step is repeated 3 times. The final precipitate is lyophilized.

B. Preparation of Purified Collagen Scaffoldings

Tissues used to prepare such scaffoldings contain various ratios of collagen/non-collagen materials. Tendon is an example of a tissue containing a high relative proportion of collagen and bovine intestinal serosa (a material used to manufacture surgical sutures) an example of one which contains significant amounts of non-collagenous impurities.

Such tissues, cleaned of fat and adherent connective tissue, are placed on suitable supports when necessary to preserve their original shape.

They are subjected to the sequential enzymatic digestion with 0.5M acetic acid containing NaCl (5%) and pepsin (2%) (1 liter per 100 g of collagenous tissue). Digestion is carried on at 4° C. with gentle agitation for 24 hrs. This procedure is repeated twice. The removal of residual enzyme and digested products is done as previously described using first an acetic acid high salt solution (0.5M acetic acid containing 5% NaCl) followed by a high salt neutral phosphate solution (0.05M NaPO$_4$ pH=7.0; 4M NaCl). Tissues are rinsed 3 times with each of these solutions.

The final washed tissue is desalted with 20% IPA and the tissue processed for further use, stored frozen or in the freeze dried state. When necessary, these tissues are crosslinked using standard chemical or physical methods. In this example it is crosslinked by soaking in a buffered glutaraldehyde solution for 7 days (0.2% glutaraldehyde in 0.02M sodium phosphate, pH=7.0).

C. Alternate Procedure to Obtain Tissue-Derived Collagen Scaffoldings

A collagen rich tissue, in this example a segment of bovine aorta is subjected for a period of 2 days (1 to 4 days) to sequential enzymatic digestion in a solution containing 0.5% acetic acid and consistently changing concentrations of NaCl, ranging between 1% and 5%. For this purpose a gradient device is designed to cause the concentration of NaCl to fluctuate between these 2 extremes (1% and 5%). Such changes in ionic strength allow for swelling and deswelling of the collagen fibrils, thus allowing greater access of the enzyme to the interstices of the fibrils and fiber bundles assuring the removal of essentially all the non-collagenous remnants, without disrupting the molecular packing within the fibrils. The changing gradients are generated by alternating the rates at which the 2 stock solutions 0.5% acetic acid - 1% NaCl and 0.5% acetic acid 5% NaCl, are delivered to the container holding the tissue specimen. A preferred cycling time from 1% NaCl to 5% NaCl and back to 1% NaCl should take approximately 2 hours. Such effect is achieved by the aid of a simple pumping device attached to a constant level reservoir.

Removal of residual enzyme and digested products is done as previously described using first an acetic acid high salt solution (0.5M acetic acid containing 5% NaCl) followed by a high salt neutral phosphate solution (0.05M NaPO$_4$ pH=7.0; 4M NaCl). Tissues are rinsed 3 times with each of these solutions.

It is the subject matter of this invention to provide a simple, easy to accomplish procedure to generate large amounts of purified collagen, in a matrix or powdered configuration. The collagen in question can be either transformed into monomeric or polymeric suspensions or retained in the native fibrillar organization as found in the original tissue from which it was derived. It can be subsequently crosslinked to modulate its degree of resorption using standard crosslinking technology.

Immunogenicity is significantly reduced by eliminating non-collagenous tissue contaminants and telopeptide extensions while preserving the natural properties of collagen (i.e. cell compatibility, hemostasis) which are maximized due to the retention of the native configuration of the molecules within the fibrils.

The materials described in the above examples and obtained using the outlined procedures may be used to provide a purified network of collagen fibers which retain their native characteristics (fibril diameter, orientation, packing, etc.) or as a source of purified collagen which can then be transformed into powder, sheets, filaments, blocks, or other suitable configurations. While the preferred embodiments have been described, various modifications and substitutions may be made thereto without departing from the spirit and scope of this invention. Accordingly, it is to be understood that the present invention has been described by way of illustration and not limitation.

What is claimed is:

1. A method for producing a pure collagen composition from collagenous animal tissue containing non-collagenous material, said collagen composition consisting essentially of a network of solid fibril collagen in its native structure and having alpha chains in a triple helical configuration, which comprises (a) forming a proteolytic enzyme digesting solution having suspended therein animal tissue containing a network of solid fibril collagen in its native structure and having alpha chains in a triple helical configuration and non-collagenous material, said proteolytic enzyme digesting solution consisting essentially of a proteolytic enzyme and from 1% to 5% salt, (b) maintaining said suspended animal tissue in said proteolytic enzyme solution until said non-collagenous material is digested, and (c) separating the residual enzyme and non-collagenous material from the solid collagen network.

2. The method of claim 1 wherein said salt is NaCl.

3. The method of claim 2 wherein the concentration of NaCl is about 5%.

4. The method of claim 2 wherein the concentration of NaCl alternates in a cyclic fashion between 1% and 5%.

5. A method according to claim 1 wherein step (b) is conducted at a temperature between about 4° C. to 1° C.

6. A method according to claim 1 wherein said proteolytic enzyme is pepsin and the proteolytic enzyme digesting solution contains acetic acid.

7. A method according to claim 1, which includes the following step: (d) cross-linking said solid collagen network.

8. The method of claim 7 where the cross-linking agent is a salt of chromium.

9. The method of claim 7 where the cross-linking agent is natural tannin.

10. The method of claim 7 where the cross-linking agent is an aldehyde.

11. The process of claim 1 wherein said collagenous animal tissue is a member selected from the group consisting of tendons, heart valves, pericardium, ligaments, skin, blood vessels, fascia, cartilage and intestine.

* * * * *